(12) United States Patent
Raczek et al.

(10) Patent No.: US 6,693,216 B2
(45) Date of Patent: Feb. 17, 2004

(54) CALCIUM DOUBLE SALTS

(75) Inventors: Nico N. Raczek, Kelkheim (DE);
Christoph Mollenkopf, Frankfurt am Main (DE)

(73) Assignee: Nutrinova Nutrition Specialties & Food Ingredients GmbH, Wiesbaden (DE)

( * ) Notice: Subject to any disclaimer, the term of this patent is extended or adjusted under 35 U.S.C. 154(b) by 243 days.

(21) Appl. No.: 09/973,565

(22) Filed: Oct. 9, 2001

(65) Prior Publication Data

US 2002/0068113 A1 Jun. 6, 2002

(30) Foreign Application Priority Data

Oct. 11, 2000 (DE) .......................... 100 50 246

(51) Int. Cl.$^7$ .............................. C07C 51/42
(52) U.S. Cl. ................. 562/598; 426/133; 426/321; 426/330; 426/330.3; 426/330.5; 426/331; 426/335; 426/582
(58) Field of Search .................. 562/598; 426/133, 426/321, 330, 330.2, 330.5, 331, 335, 582

(56) References Cited

U.S. PATENT DOCUMENTS 5,075,499 A    12/1991    Walsdorf et al.

FOREIGN PATENT DOCUMENTS

| DE | 197 39 319 A1 | 3/1999 |
|----|---------------|--------|
| EP | 0 590 856 A1  | 4/1994 |
| EP | 0 608 975 A1  | 8/1994 |
| GB | 467080        | 6/1937 |

OTHER PUBLICATIONS

XP002190098 Abstract, Tashk Agric. Irrig, Aug. 7, 1982.

*Antimicrobial Food Additives Characteristics, Uses, Effects* by Erich Lück and Martin Jager, ($2^{nd}$ revised and enlarged edition, Springer).

*Primary Examiner*—Paul J. Killos
(74) *Attorney, Agent, or Firm*—ProPat, L.L.C.

(57) ABSTRACT

The present invention relates to calcium double salts having good preservative properties. Said salts can be used in foods, feeds, pet food, cosmetics and pharmaceuticals, food-contact items, silage, brewers' spent grains, pomace, food wastes, brewers' yeast, distillation residues and other wastes from the food industry or for leather treatment. These substances exhibit a considerably extended shelf life after addition of, or treatment with, one of the calcium double salts.

19 Claims, 2 Drawing Sheets

CALCIUM DOUBLE SALTS

The present invention relates to stable calcium double salts which contain, in one molecule, one calcium atom (cation) and one radical each of two different organic acids (anion) in the same stoichiometric ratio, preferably acids such as formic acid, acetic acid, propionic acid, sorbic acid and benzoic acid. In addition, the invention relates to formulations that comprise the double salts and a stabilizer and/or a formulating aid.

BACKGROUND OF THE INVENTION

The invention further relates to a process for preparing the double salts, and to the use of the salts in foods, cosmetics and drugs, food-contact articles, feeds, for example in silage, brewer's spent grains, pomace, food wastes, brewer's yeast, distillation residues and other wastes from the food industry, or as preservative in industrial products.

Antimicrobial substances which are less physiologically harmful are increasingly replacing substances which are hazardous to health or the environment, for example antibiotics, formaldehyde-releasing substances, halogenated substances, boric acid derivatives, and many others, in foods, feeds, pet food, cosmetics and drugs, food-contact articles, silage, brewer's spent grains, pomace, food waste, brewer's yeast, distillation residues and other wastes from the food industry or in leather treatment. Substances which are less physiologically hazardous include the classic preservatives, in particular sorbic acid, propionic acid or benzoic acid. These organic acids are used in particular in the food industry *Antimicrobial Food Additives Characteristics, Uses, Effects* by Erich Lück and Martin Jager, (2$^{nd}$ revised and enlarged edition, Springer)

However, increasingly, mixtures of organic acids are being used. A frequent disadvantage is the liquid state, their volatility or poor solubility even of some of their sodium salts, potassium salts, calcium salts or magnesium salts. Poor miscibility or incompatibility of these acids is frequently observed. Thus, for example, mixtures of formic acid and benzoic acid exhibit a rapid brown discoloration, which is possibly due to oxidation reactions.

Preservative acids generally act in their undissociated form. This dependence on the pH gives the necessity of using high concentrations of some preservatives in less acidic foods which, for example in the case of the use of propionic acid in bread, can very rapidly become noticeable by disadvantageous sensory properties.

Differing product properties of the products to be preserved, in particular differing consistency and differing pHs lead to the fact that there is no generally optimum preservative, but that product-specific solutions in preservative are required (M. Jager and E. Lück: see above). However, in many cases, such solutions mean that, in addition to one preservative, other substances must be added, and there is thus the necessity, for example, of adding various preservatives one after the other and keeping stores of them.

DE-A 197 39 319 describes acid-impregnated carboxylic acid salts, inter alia, or calcium formate impregnated with propionic acid. The invention only relates to the mixing of salts and acids, the acid physically adsorbing to the salt, with no chemical reaction occurring.

It was an object of the present invention to prepare a defined product that combines the advantages of two preservative acids. In particular, a storage-stable product was to be prepared that can withstand without loss relatively long transport and storage times, or poor storage conditions. In addition, it was an object to prepare products that can readily be employed in the food or related industries.

SUMMARY OF THE INVENTION

This object is achieved by calcium double salts containing two different acid units per double salt molecule. It has been found that, in addition to the calcium salts of organic acids which have long been known, a whole series of calcium double salts containing two different acids in the molecule can be prepared, in which various combinations of acid anions are possible.

The invention therefore relates to calcium double salts of the formula I:

$$Ca(R^1)(R^2) \tag{I}$$

where $R^1$ and $R^2$ are different and are each OOC—$R^3$, where $R^3$=saturated or monounsaturated or polyunsaturated $C_1$–$C_5$-alkyl, $C_1$–$C_5$-hydroxyalkyl or phenyl. Preference is also given to compounds in which customary preservative acids are used, that is to say compounds of the formula (I), where $R^3$ is methyl, ethyl, hydroxyethyl (=lactate anion), propyl, 1,3-hexadienyl (=sorbate anion) or phenyl. Very particularly preferably, $R^1$ is propionate and $R^2$ is sorbate.

DETAILED DESCRIPTION OF THE INVENTION

Figure 1:
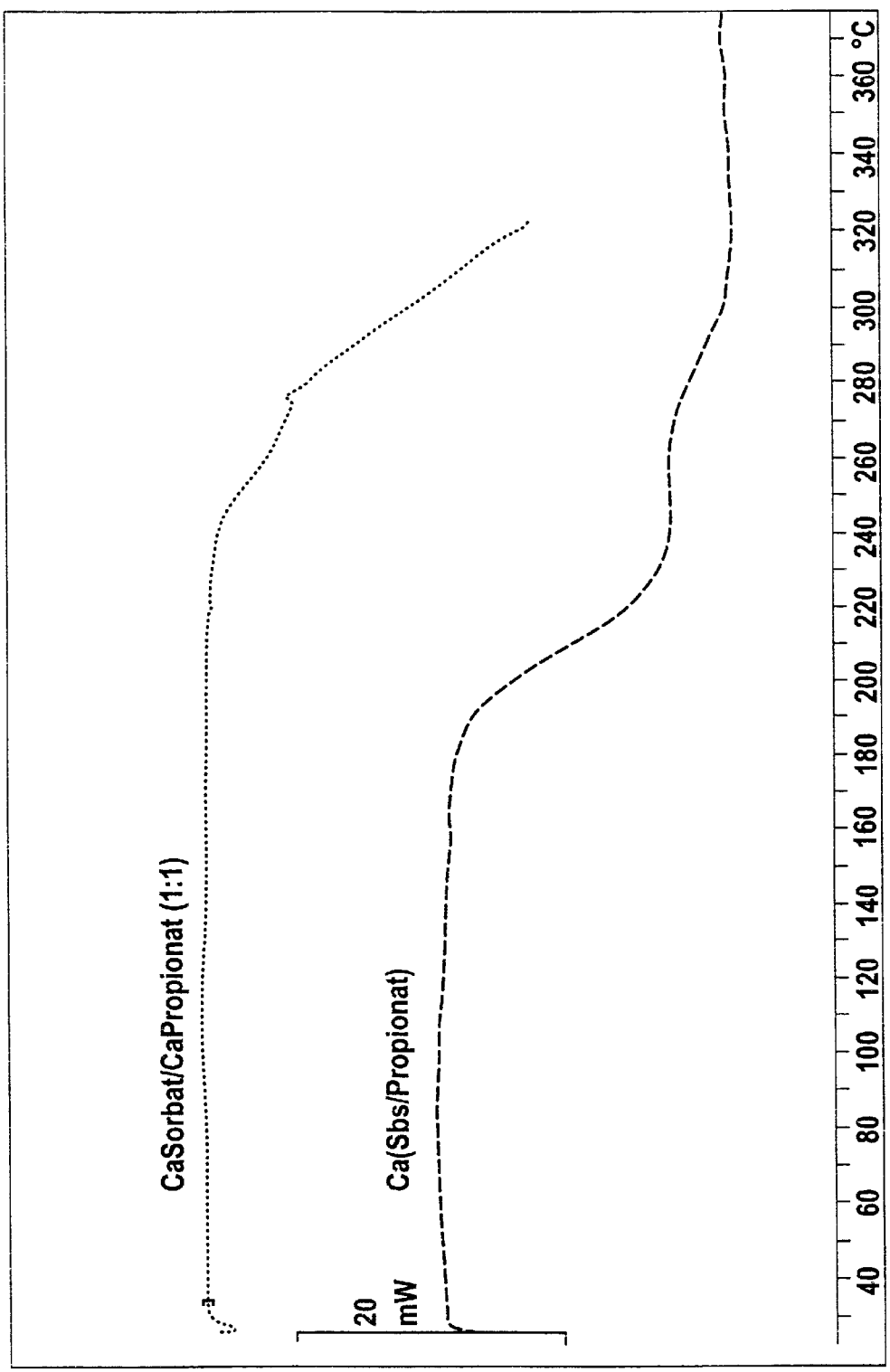
FIG. 1 is a graphical representation of differential scanning calorimetry results for the calcium double salt of sorbic acid and propionic acid on comparison to 1:1 mixtures of the calcium salts.

If, in contrast, attempts are made to prepare sodium salts or potassium salts, depending on the molar ratio of the starting materials used (for example in the reaction of sodium acetate with lactic acid, or of potassium sorbate with propionic acid, or of sodium benzoate with acetic acid), only products which are inadequately stable and are defined are obtained. These products liquefy and turn dark brown even after a short time without sufficiently high amounts of carrier/stabilizer, so that here virtually no usable product can be produced. This also relates to the impregnated salt described in DE 197 39 319 which, without appropriate additives, form lumps and at room temperature, after a short storage period, show a brown discoloration. Surprisingly, the inventive calcium double salts do not exhibit this behavior.

One possible method of preparing these double salts is reacting one alkali metal salt, preferably a sodium salt or potassium salt of the one acid, with the calcium salt of the other acid. Preferably, calcium salts of the formic acid, acetic acid, propionic acid, sorbic acid and benzoic acid are used. The resultant defined calcium double salts display an excellent stability. In addition, there is the possibility of reacting two acids in stoichiometric ratios with calcium hydroxide solution. Both methods produce, after isolation and drying, defined white, amorphous or very fine crystalline powders which contain, in one molecule, one calcium atom and one (deprotonated) radical of each of two different organic acids in the same stoichiometric ratio. These double salts, in contrast to impregnated salts and products obtained when alkali metal salts of the same acid are used, are very stable and do not exhibit brown discoloration even after relatively long storage.

In the preparation of the double salts, preferably, aqueous, saturated solutions are employed at temperatures between 15 and 40° C., preferably between 20 and 25° C. The molar ratio of the salts to be mixed is from 1:0.2 to 1:1, preferably from 1:0.35 to 1:0.5. The time for mixing and removing precipitate is in total between 1 and 15 min, preferably between 2 and 10 min. The products can be dried between 25 and 100° C., preferably between 30 and 60° C., and at 30 to 500 hPa, preferably between 80 and 150 hPa. Calcium salts of the individual acids can be formed in relatively small amounts as byproduct.

The defined double salts of, preferably, formic acid, acetic acid, propionic acid, sorbic acid, benzoic acid exhibit excellent antimicrobial activity. Microorganisms are inhibited particularly well by double salts of two marked preservative acids, for example by the calcium double salt of sorbic and propionic acids.

The inventive double salts may be used in the sectors where customary preservatives are used. In addition to the preservative action, with the inventive salts, when calcium-sensitive thickeners and gelating agents are used simultaneously, solidification is achieved for which in other cases calcium salts must be specifically added. The fields of use include:

Drinks

The inventive double salts can be used to preserve soft drinks and alcoholic drinks and concentrates used for drink production. They prevent, in particular, unwanted fermentations due to yeasts. Concentrations used are 0.05–5 g/kg, preferably 0.1 to 1 g/kg.

Fruit Products, Dried Fruit, Jams and Marmalades

An expedient concentration used is about 0.1 to 5 g/kg, preferably 0.25 to 2 g/kg. Especially in the case of low-sugar and thickener-containing products, not only is microbiological stabilization achieved, but also the calcium required for the gelation of low-esterified pectins can also be supplied. The double salts should expediently be added, in the case of heated products, towards the end of the heating process, especially if losses of volatile acids are possible.

Acid Vegetables, Prepared Salads and Spiced Sauces

In the case of acid vegetable preserves such as pickled gherkins, mixed pickles and the like and lactic-fermented vegetables such as sauerkraut and olives, the inventive salts are added to the covering liquids in amounts of up to 0.1 to 5 g/kg, preferably 0.25 to 3 g/kg. In the same concentration range, they are also suitable for use in prepared salads, spiced sauces and related products such as mustard.

Bakery Products and Doughs

The inventive double salts may be used without a problem in bakery products of the most varied types that are susceptible to decay, bakery fillings, part-baked and prebaked products and prepared doughs. Depending on the product and the desired increase in shelf life, amounts up to 0.5 to 5 g/kg are expedient for this.

For use in fine bakery products, in particular in bakery products with not baked fillings based on alginates, thermally reversible gels can be obtained. Also, similar effects can be achieved with the use of starch or other thickeners. Fillings of all types in and on bakery products, meringues, chocolate sauces, salad sauces and ice cream can not only have their microbiological stability considerably increased, but other stabilizing or destabilizing effects can be achieved with the use of calcium double salts. For this purpose, addition of 0.5 to 5 g/kg to the corresponding products is necessary. The amount added in this case essentially depends on the concentration of alginates, starch and other thickeners. The inventive salt can be added to a dry premix which is prepared into a finished form at a later time, generally by adding milk, cream or water, or may be added to certain preparations, e.g. homogeneously dispersed in fat or egg, whereby the foam strength or stability of mix are increased.

Cheese

Addition of 0.5 to 2 g/kg, based on the entire cheese, of the inventive salts is generally sufficient to preserve matured cheeses. Addition of the inventive double salts to the salt bath keeps the cheese thus treated mold-free for several weeks. Preferably, 0.5–10 g/l of the salts, depending on the solubility, are added per day to the salt baths of hard cheeses. Surface treatment using aqueous solution by dipping or spraying with aqueous solutions or suspensions of the salts at a concentration of 10 g/l and post-treatment at intervals of 1 to 5 weeks keeps maturing cheese free from mold. In the case of cheeses which do not permit spray treatment, it is also possible to apply a suspension which has been made viscous or to apply the dry salts.

In the case of process cheese, these salts can be added together with the emulsifying salts.

In the same manner, in the case of curd cheese and fermented milk products, addition of up to 0.5 to 2 g/kg of the salts achieves good extension of shelf life.

Fat Emulsions

For use in fat emulsions such as margarine, mayonnaise, salad sauces and dressings, preferably, more readily soluble double salts are used. The customary amounts used are up to 0.25 to 3 g/kg. They are expediently added to the water phase before emulsification.

Meat Products and Fish Products

Meat products and fish products, for example pates and fish marinades may, in most cases, be preserved by amounts up to 0.5 to 10 g/kg of the inventive salts. In the case of products which are particularly perishable, such as boiled crustacea, up to 10 g/kg may be necessary, however.

Surface Treatment and Coatings

The surface treatment of foods, for example meat products such as ripened sausages or ham and dry meat, can be performed in the same manner and using the same amounts as in the case of ripened cheeses. To form coatings on foods, such as coating packaging media, expediently, carriers or coating agents or film-forming agents are used. Substances which are suitable for this are, in particular, starch, starch ethers, oxidized or degraded starch, cellulose ethers, alginates, gellan, gelatin and polyvinyl alcohol.

Packaging

By introducing the calcium double salts into coatings of foods or industrial products and packaging materials, a fungistatic effect is achieved. Using about 1 to 10 g of calcium double salt/$m^2$, in the case of packaging film or packaging paper a protective action against mold formation below the packaging is achieved, if this is in direct contact with the packaged material. The coated packaging can be used not only to increase the shelf life of fresh foods such as meat, fish, etc., but also for packaged foods of the most varied types, such as bakery products, pasta and convenience food in the broadest sense.

Animal Feed and Other Products Suitable as Feedstuffs

The addition of the inventive salts also increases the shelf life of animal feed. This also includes products which are suitable for use as feedstuffs, for example silages, brewer's spent grains, pomace, brewer's yeast, distillation residue and various food wastes. The salts can be added to the feed dry in suitable powder form, they can be added before further processing (for example extrusion), or can be sprayed in solution or added dissolved in a mixture. For these purposes, concentrations up to 0.2 to 50 g/kg, preferably 0.5 to 5 g/kg, are employed.

Cosmetics and Drugs

To preserve aqueous cosmetics and pharmaceutical products (including drugs), to increase the shelf life the inventive calcium double salts are added to these at a concentration of 0.2 to 50 g/kg, preferably 0.5 to 10 g/kg, in particular 0.5 to 5 g/kg.

Food-Contact Articles and Industrial Products

To preserve food-contact articles, including those which are intended for cleaning and maintaining machinery and apparatus in the food industry, and for microbially susceptible industrial products, the inventive calcium double salts can be added at concentrations of up to 0.1 to 50 g/kg, preferably 0.5 to 10 g/kg.

The invention is illustrated by the following examples:

EXAMPLE 1

Preparation of a Calcium Double Salt of Sorbic Acid and Acetic Acid 158 g (1 mol) of calcium acetate are dissolved in 420 ml of water. To this solution are added, at 25° C., a solution of 56 g (0.37 mol) of potassium sorbate in 60 ml of water.

During the addition a precipitate forms immediately which is filtered off after 5 min. The precipitate is dried to constant weight at 100 mbar and 50° C. 88% pure calcium acetate sorbate is obtained as a white powder in 73% yield.

EXAMPLE 2

Preparation of a Calcium Double Salt of Sorbic Acid and Propionic Acid 186 g (1 mol) of calcium propionate are dissolved in 500 ml of water. To this solution are added, at 25° C., a solution of 56 g (0.37 mol) of potassium sorbate in 60 ml of water. During addition a precipitate forms which is filtered off after 2 min. The precipitate is dried to constant weight at 150 mbar and 50° C. 90% pure calcium propionate sorbate is obtained as a white powder in 75% yield.

EXAMPLE 3

Preparation of a Calcium Double Salt of Propionic Acid and Benzoic Acid 186 g (1 mol) of calcium propionate are dissolved in 500 ml of water. To this is added a solution of 57.6 g (0.4 mol) of sodium benzoate in 70 ml of water. The precipitate which forms immediately is filtered off after 2 min and is then dried as in example 2. 75 g of the double salt are obtained as a white powder.

EXAMPLE 4

Preparation of a Calcium Double Salt of Sorbic Acid and Formic Acid 130 g (1 mol) of calcium formate are dissolved in 550 ml of water. To this is added a saturated solution of 60 g (0.4 mol) of potassium sorbate. The precipitate which forms immediately is filtered off after 5 min and is then dried as in example 1. 60 g of the double salt are obtained as a white powder.

EXAMPLE 5

The prepared double salts are compared with mixtures of the corresponding calcium salts using differential scanning calorimetry (DSC). Fundamentally changed melting points or decomposition points were found.

Figure 2:
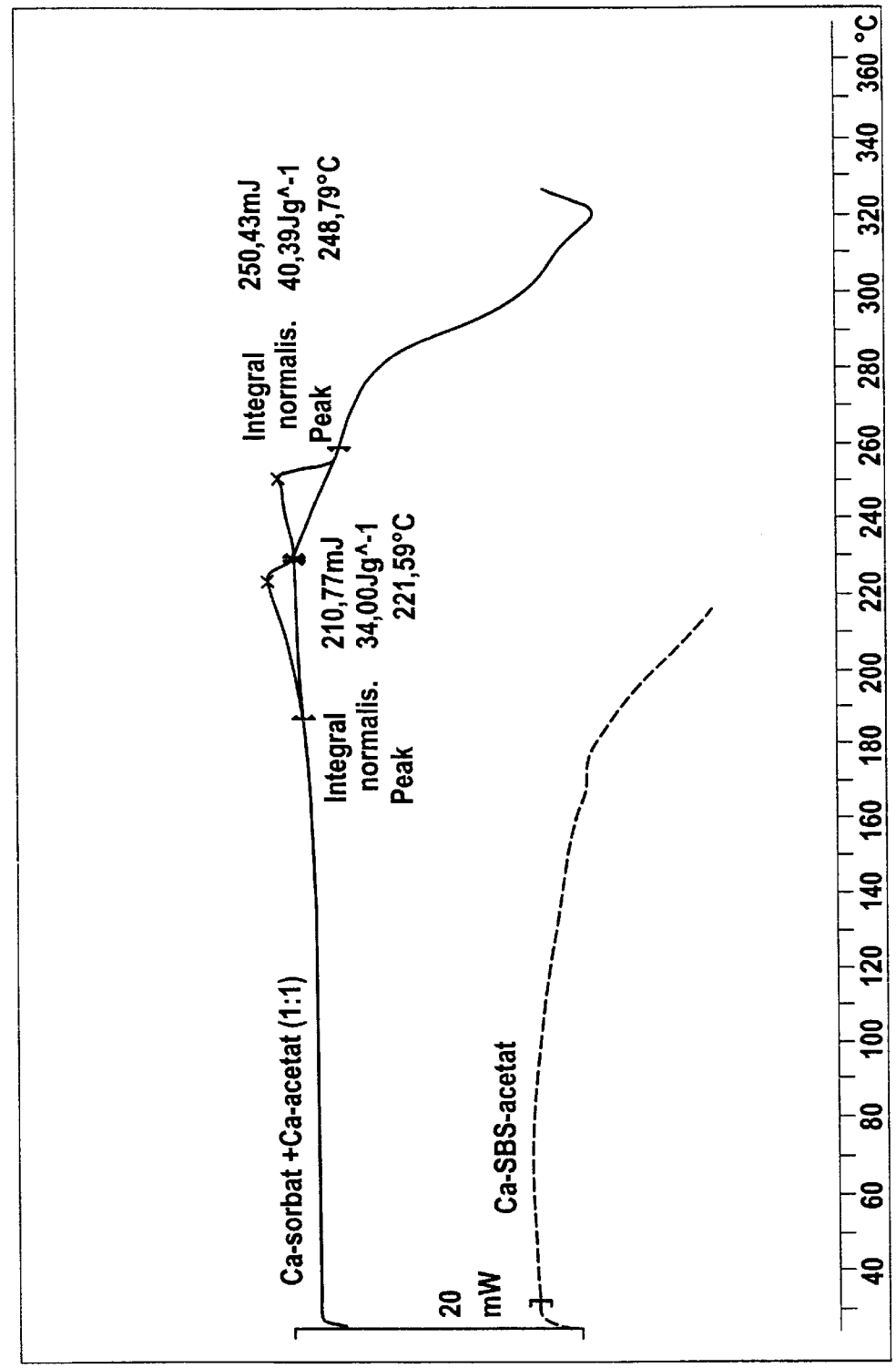
FIG. 2 is a graphical representation of differential scanning calorimetry results for the calcium double salt of sorbic acid and acetic acid in comparison to 1:1 mixtures of the calcium salts.

The appendix gives the DSC charts of
1) the calcium double salt of sorbic acid and propionic acid (FIG. 1) and
2) the calcium double salt of sorbic acid and acetic acid, in each case compared with 1:1 mixtures of the calcium salts (FIG. 2).

EXAMPLE 6

Shelf Life of the Calcium Double Salts

Salts prepared as in example 1 were dried, stored under the specified conditions without the addition of other substances and checked at regular intervals visually for discoloration:

| Type of salt | Time after yellow-brown discoloration of the powder, sealed, dark at 25° C./7° C. under sunlight at 25° C./7° C. | Time after yellow-brown discoloration of a 1% strength aqueous solution, sealed, dark at 25° C./7° C. under sunlight at 25° C./7° C. |
|---|---|---|
| Calcium double salt of sorbic acid and acetic acid | 12 months />12 months<br>12 months />12 months | >12 months />12 months<br>12 months />12 months |
| Corresponding "impregnated salts" as in DE 197 39 319 | 2 months/2 months<br>4–5 weeks/2 months | 3–4 weeks /—<br>3–4 weeks/— |
| Calcium double salt of benzoic acid and propionic acid | 7 months/12 months<br>8 months /12 months | 8 months /12 months<br>7–8 months/12 months |
| Corresponding "impregnated salts" as in DE 197 39 319 | 5 weeks/7 weeks<br>6 weeks/7 weeks | 6 weeks/8 weeks<br>7 weeks/7 weeks |
| Calcium double salt of sorbic acid and propionic acid | 12 months/>12 months<br>12 months/12 months | >12 months/>12 months<br>12 months/12 months |
| Corresponding "impregnated salts" as in DE 197 39 319 | 1–2 weeks/4–5 weeks<br>1–2 weeks/3–4 weeks | 2–3 weeks/4–5 weeks<br>3–4 weeks/4–5 weeks |
| Calcium double salt of formic acid and sorbic acid | >12 months />12 months<br>12 months/>12 months | 12 months/>12 months<br>12 months/>12 months |
| Corresponding "impregnated salts" as in DE 197 39 319 | 4–5 weeks/2 months<br>4–5 weeks/2 months | 3–4 weeks/3–4 weeks<br>4–5 weeks/— |

The impregnated salts described in DE 19 739 319 were markedly discolored, generally at the latest after 2 months, in all cases under these conditions, without addition of stabilizers.

EXAMPLE 7

Test of Preservative Action

Part I:

The preservative action of the double salts (here: part I, comparison between calcium double salt of sorbic and propionic acids and potassium sorbate) was tested in a model food. For this an apple juice adjusted to pH 4.5 was used. The test microorganisms were used to prepare microorganism suspensions in NaCl-peptone buffer having a target content of $10^6$. CFU/ml of microorganism suspension. 50 ml of sample or control in each case were inoculated with 0.5 ml of the individual microorganism mixtures, homogenized and incubated at 25° C. The following microorganism suspensions were added as equal proportions for the loading:

| Microorganism mixture | CFU/ml |
|---|---|
| *Lactobacillus acidophilus* DSM 20079 | $1.3 \times 10^6$ |
| *Lactobacillus delbrückii sp. bulgaricum* DSM 20081 | $2.2 \times 10^6$ |
| *Leuconostoc mesenteroides* DSM 20343 | $2.3 \times 10^6$ |
| Total lactic acid bacteria: | $1.9 \times 10^6$ |
| *Clostridium perfringens* DSM 63442 | $1.1 \times 10^6$ |
| *Clostridium sporogenes* ATCC 10543 | $1.4 \times 10^6$ |
| Total clostridia: | $1.2 \times 10^6$ |
| *Bacillus cereus* DSM 345 | $1.2 \times 10^6$ |
| *Bacillus subtilis* DSM 374 | $1.8 \times 10^6$ |

-continued

| Microorganism mixture | CFU/ml |
|---|---|
| Total bacilli:<br>Total thermophilic bacilli | $1.5 \times 10^6$ |
| *Bacillus stearothermophilus* DSM 5934 | $1.3 \times 10^6$ |
| *Acetobacter pasteurianus* DSM 3509 | $2.7 \times 10^6$ |
| *Acetobacter aceti* DSM 3508 | $2.1 \times 10^6$ |
| *Gluconobacter oxidans* DSM 3504 | $2.1 \times 10^6$ |
| Total acetic acid bacteria: | $2.3 \times 10^6$ |
| *Saccharomyces cerevisiae* DSM 70451 | $2.8 \times 10^6$ |
| *Zygosaccharomyces rouxii* DSM 7525 | $1.9 \times 10^6$ |
| *Candida albicans* ATCC 10231 | $3.6 \times 10^6$ |
| *Brettanomyces naardensis* CBS 733 | $2.3 \times 10^6$ |
| *Pichia anomala* CBS 1683 | $2.0 \times 10^6$ |
| Total yeasts | $2.5 \times 10^6$ |
| *Asppergillus niger* ATCC 16404 | $1.2 \times 10^6$ |
| *Cladosporium herbarum* ATCC 63442 | $1.8 \times 10^6$ |
| *Fusarium* oxysporum | $1.6 \times 10^6$ |
| *Penicillium chrysogenum* DSM 895 | $2.1 \times 10^6$ |
| Total molds<br>microorganism mixture I | $1.7 \times 10^6$ |
| *Talaromyces flavus* CBS 31763 | $1.9 \times 10^6$ |
| *Rhizopus stolonifer* DSM 2194 | $1.2 \times 10^6$ |
| *Mucor racemosus* CBS 11508 | $1.3 \times 10^6$ |
| Total molds<br>microorganism mixture II | $1.5 \times 10^6$ |
| *Escherichia coli* ATCC 8739 | $2.4 \times 10^6$ |
| *Klebsiella pneumoniae* ATCC 10031 | $1.8 \times 10^6$ |
| *Citrobacter diversus* | $2.6 \times 10^6$ |
| *Enterobacter aerogenes* DSM 30053 | $2.8 \times 10^6$ |
| Total Gram negative<br>microorganism mixture: | $2.4 \times 10^6$ |

-continued

| Microorganism mixture | CFU/ml |
|---|---|
| Total campylobacter | |
| *Campylobacter jejuni* DSM 4688 | $1.9 \times 10^6$ |
| *Staphylococcus aureus* ATCC 6538 | $2.4 \times 10^6$ |
| *Enterococcus faecalis* DSM 20478 | $2.9 \times 10^6$ |
| *Streptococcus mutans* DSM 50523 | $2.2 \times 10^6$ |
| *Listeria monocytogenes* ATCC 7644 | $2.8 \times 10^6$ |
| Total Gram positive microorganism mixture: | $2.6 \times 10^6$ |

To determine the number of surviving test microorganisms, 1 ml of sample material was removed in each case from the batches containing the corresponding microorganism mixture and mixed with 9 ml of peptone-water+N9 (4% Tween 80, 0.5% soybean lecithin). These test solutions and dilutions from the test solutions were streaked onto the corresponding agar or mixed as a pour plate with the corresponding nutrient agar. The incubation time and incubation temperatures are listed in the following table:

| Microorganisms | Agar | Incubation time | Incubation temperature |
|---|---|---|---|
| Lactic acid bacteria | Caso-HLT | 3 days | 32° C. |
| Clostridia | DRCM | 3 days | 32° C. |
| Bacilli | Caso-HLT | 3 days | 32° C. |
| Thermophilic bacilli | Caso-HLT | 3 days | 55° C. |
| Acetic acid bacteria | YPM-Agar | 3 days | 32° C. |
| Yeasts | Sabouraud-HLT | 3–5 days | 25° C. |
| Molds | Sabouraud-HLT | 3–5 days | 25° C. |
| Gram-negative microorganisms | Caso-HLT | 3 days | 32° C. |
| Campylobacter | Anaerocult C on CCDA | 3 days | 42° C. |
| Gram-positive microorganisms | Caso-HLT | 3 days | 32° C. |

HLT = 3% Tween 80, 0.5% lecithin, 0.1% histidine

The number of surviving microorganisms was determined 1 day (24 h), 3 days, 1 and 2 weeks after inoculation. The following results were obtained:

Apple Juice Without Additives

Content of Surviving Microorganisms per Gram of Sample (CFU/g) After Contamination

| | Number of surviving microorganisms per g of contaminated sample in the batch after: | | | | | |
|---|---|---|---|---|---|---|
| Microorganisms | Lactic acid bacteria | Clostridia | Bacilli | Thermophilic bacilli | Acetic acid bacteria | Yeasts |
| Inoculation | $1.9 \times 10^4$ | $1.4 \times 10^4$ | $1.5 \times 10^4$ | $1.3 \times 10^4$ | $2.3 \times 10^4$ | $2.5 \times 10^4$ |
| 1 day | $2.1 \times 10^6$ | $1.8 \times 10^3$ | $1.7 \times 10^3$ | $2.0 \times 10^4$ | $2.9 \times 10^5$ | $5.2 \times 10^5$ |
| 3 days | $>3.0 \times 10^6$ | 750 | 900 | 250 | $>3.0 \times 10^6$ | $2.7 \times 10^6$ |
| 7 days | $>3.0 \times 10^6$ | 750 | 750 | 15 | $>3.0 \times 10^6$ | $>3.0 \times 10^6$ |
| 14 days | $3.6 \times 10^6$ | $3.9 \times 10^3$ | 800 | 15 | $2.1 \times 10^6$ | $2.1 \times 10^7$ |

Content of Surviving Microorganisms per Gram of Sample (CFU/g) After Contamination

| | Number of surviving microorganisms per g of contaminated sample in the batch after: | | | |
|---|---|---|---|---|
| Microorganisms | Molds I | Molds II | Gram-negative bacteria | Gram-positive bacteria |
| Inoculation | $1.7 \times 10^4$ | $1.5 \times 10^4$ | $2.4 \times 10^4$ | $2.6 \times 10^4$ |
| 1 day | $5.5 \times 10^4$ | $2.5 \times 10^4$ | $5.5 \times 10^5$ | $6.0 \times 10^4$ |
| 3 days | $1.2 \times 10^5$ | $1.5 \times 10^4$ | $>3.0 \times 10^6$ | $1.1 \times 10^6$ |
| 7 days | $1.3 \times 10^4$ | $7.0 \times 10^3$ | $2.7 \times 10^6$ | $>2.0 \times 10^6$ |
| 14 days | $1.6 \times 10^4$ | $8.5 \times 10^3$ | $3.2 \times 10^7$ | $1.3 \times 10^6$ |

Addition of 1 g/l of Calcium Double Salt of Sorbic Acid and Propionic Acid

Content of Surviving Microorganisms per Gram of Sample (CFU/g) After Contamination

| | Number of surviving microorganisms per g of contaminated sample in the batch after: | | | | | |
|---|---|---|---|---|---|---|
| Microorganisms | Lactic acid bacteria | Clostridia | Bacilli | Thermophilic bacilli | Acetic acid bacteria | Yeasts |
| Inoculation | $1.9 \times 10^4$ | $1.4 \times 10^4$ | $1.5 \times 10^4$ | $1.3 \times 10^4$ | $2.3 \times 10^4$ | $2.5 \times 10^4$ |
| 1 day | $4.0 \times 10^4$ | $1.3 \times 10^3$ | $2.3 \times 10^4$ | $1.1 \times 10^3$ | $7.5 \times 10^4$ | $8.5 \times 10^4$ |
| 3 days | $3.2 \times 10^5$ | 800 | $1.4 \times 10^3$ | <100 | $2.1 \times 10^6$ | $5.0 \times 10^4$ |
| 7 days | $2.4 \times 10^3$ | 310 | $1.3 \times 10^3$ | 10 | $2.9 \times 10^6$ | $1.2 \times 10^3$ |
| 14 days | 130 | 55 | 50 | 5 | $1.1 \times 10^6$ | 10 |

Content of Surviving Microorganisms per Gram of Sample (CFU/g) After Contamination

| Microorganisms | Molds I | Molds II | Gram-negative bacteria | Gram-positive bacteria |
|---|---|---|---|---|
| Inoculation | $1.7 \times 10^4$ | $1.5 \times 10^4$ | $2.4 \times 10^4$ | $2.6 \times 10^4$ |
| 1 day | $4.0 \times 10^3$ | $1.1 \times 10^3$ | $3.5 \times 10^4$ | $7.0 \times 10^4$ |
| 3 days | 700 | 80 | $1.7 \times 10^3$ | $7.0 \times 10^3$ |
| 7 days | <100 | 50 | 900 | 400 |
| 14 days | <10 | <10 | <10 | <10 |

Addition of 1 g/l of Potassium Sorbate

Content of Surviving Microorganisms per Gram of Sample (CFU/g) After Contamination

| Microorganisms | Molds I | Molds II | Gram-negative bacteria | Gram-positive bacteria |
|---|---|---|---|---|
| Inoculation | $1.7 \times 10^4$ | $1.5 \times 10^4$ | $2.4 \times 10^4$ | $2.6 \times 10^4$ |
| 1 day | $5.0 \times 10^4$ | $2.0 \times 10^4$ | $2.9 \times 10^4$ | $5.5 \times 10^4$ |
| 3 days | <100 | 400 | $1.5 \times 10^3$ | $7.0 \times 10^3$ |
| 7 days | <10 | <100 | 350 | <100 |
| 14 days | <10 | <10 | <10 | <10 |

The results of these tests show that the calcium double salt of propionic acid and sorbic acid acts well and persistently against all microorganisms used, except for bacilli. In the case of contamination, this double salt acts surprisingly better than potassium sorbate (used at the same concentration), in particular against lactic acid bacteria, thermophilic bacilli, yeasts and some molds (molds group II).

Test of Preservative Action

Part II:

In a second experiment, the preservative action of the double salts (here: comparison between calcium double salt of sorbic and acetic acids or formic acid with the corresponding calcium salts) was tested in the above described model food.

The following microorganism suspensions were added at equal proportions for the contamination:

Number of surviving microorganisms per g of contaminated sample in the batch after:

| Microorganisms | Lactic acid bacteria | Clostridia | Bacilli | Thermophilic bacilli | Acetic acid bacteria | Yeasts |
|---|---|---|---|---|---|---|
| Inoculation | $1.9 \times 10^4$ | $1.4 \times 10^4$ | $1.5 \times 10^4$ | $1.3 \times 10^4$ | $2.3 \times 10^4$ | $2.5 \times 10^4$ |
| 1 day | $1.3 \times 10^4$ | $1.1 \times 10^3$ | $1.4 \times 10^3$ | $1.6 \times 10^3$ | $1.7 \times 10^4$ | $2.7 \times 10^5$ |
| 3 days | $1.2 \times 10^6$ | 450 | (<100) | 900 | $4.3 \times 10^5$ | $1.1 \times 10^4$ |
| 7 days | $1.7 \times 10^6$ | 160 | $1.4 \times 10^3$ | <100 | $1.3 \times 10^3$ | $6.0 \times 10^2$ |
| 14 days | $1.2 \times 10^7$ | 250 | $1.3 \times 10^3$ | <10 | $2.7 \times 10^5$ | <10 |

| Microorganism mixture | CFU/ml |
|---|---|
| *Lactobacillus acidophilus* DSM 20079 | $2.7 \times 10^6$ |
| *Lactobacillus delbruckii sp. bulgaricum* DSM 20081 | $2.5 \times 10^6$ |
| *Leuconostoc mesenteroides* DSM 20343 | $2.9 \times 10^6$ |
| Total lactic acid bacteria: | $2.7 \times 10^6$ |
| *Clostridium perfringens* DSM 63442 | $2.9 \times 10^6$ |
| *Clostridium sporogenes* ATCC 10543 | $2.9 \times 10^6$ |
| Total clostridia: | $2.9 \times 10^6$ |
| *Bacillus cereus* DSM 345 | $3.4 \times 10^6$ |
| *Bacillus subtilis* DSM 374 | $3.2 \times 10^6$ |
| Total bacilli: | $3.3 \times 10^6$ |
| Total thermophilic bacilli | |
| *Bacillus stearothermophilus* DSM 5934 | $1.3 \times 10^6$ |
| *Acetobacter pasteurianus* DSM 3509 | $2.4 \times 10^6$ |
| *Acetobacter aceti* DSM 3508 | $2.3 \times 10^6$ |
| *Gluconobacter oxidans* DSM 3504 | $3.8 \times 10^6$ |
| Total acetic acid bacteria: | $2.8 \times 10^6$ |
| *Saccharomyces cerevisiae* DSM 70451 | $2.6 \times 10^6$ |
| *Zygosaccharomyces rouxii* DSM 7525 | $2.9 \times 10^6$ |
| *Candida albicans* ATCC 10231 | $3.1 \times 10^6$ |

-continued

| Microorganism mixture | CFU/ml |
|---|---|
| *Brettanomyces naardensis* CBS 733 | $2.5 \times 10^6$ |
| *Pichia anomala* CBS 1683 | $1.9 \times 10^6$ |
| Total yeasts | $2.6 \times 10^6$ |
| *Aspergillus niger* ATCC 16404 | $2.9 \times 10^6$ |
| *Cladosporium herbarum* ATCC 63442 | $1.6 \times 10^6$ |
| *Fusarium oxysporum* | $2.1 \times 10^6$ |
| *Penicillium chrysogenum* DSM 895 | $2.2 \times 10^6$ |
| Total molds microorganism mixture I | $2.2 \times 10^6$ |
| *Talaromyces flavus* CBS 31763 | $2.7 \times 10^6$ |
| *Rhizopus stolonifer* DSM 2194 | $2.4 \times 10^6$ |
| *Mucor racemosus* CBS 11508 | $2.4 \times 10^6$ |
| Total molds microorganism mixture II | $2.5 \times 10^6$ |
| *Escherichia coli* ATCC 8739 | $2.1 \times 10^6$ |
| *Klebsiella pneumoniae* ATCC 10031 | $2.7 \times 10^6$ |
| *Citrobacter diversus* | $3.4 \times 10^6$ |
| *Enterobacter aerogenes* DSM 30053 | $2.7 \times 10^6$ |

-continued

| Microorganism mixture | CFU/ml |
|---|---|
| Total Gram-negative microorganism mixture: | $2.7 \times 10^6$ |
| *Staphylococcus aureus* ATCC 6538 | $2.4 \times 10^6$ |
| *Enterococcus faecalis* DSM 20478 | $1.8 \times 10^6$ |
| *Streptococcus mutans* DSM 50523 | $1.9 \times 10^6$ |
| *Listeria monocytogenes* ATCC 7644 | $2.3 \times 10^6$ |
| Total Gram-positive microorganism mixture: | $2.1 \times 10^6$ |

The study was otherwise carried out as described in part I. The number of surviving microorganisms was determined 1 day (24 h), 3 days, 1 and 2 weeks after inoculation. The following results were obtained:

Apple Juice Without Additives

Content of Surviving Microorganisms per Gram of Sample (CFU/g) After Contamination

| | Number of surviving microorganisms per g of contaminated sample in the batch after: | | | | | |
|---|---|---|---|---|---|---|
| Microorganisms | Lactic acid bacteria | Clostridia | Bacilli | Thermophilic bacilli | Acetic acid bacteria | Yeasts |
| Inoculation | $2.7 \times 10^4$ | $2.9 \times 10^4$ | $3.3 \times 10^4$ | $1.3 \times 10^4$ | $2.8 \times 10^4$ | $2.6 \times 10^4$ |
| 1 day | $2.4 \times 10^6$ | $4.9 \times 10^3$ | $4.5 \times 10^3$ | $4.1 \times 10^3$ | $1.2 \times 10^6$ | $2.3 \times 10^5$ |
| 3 days | $>3.0 \times 10^6$ | $2.7 \times 10^3$ | $3.4 \times 10^3$ | $2.3 \times 10^3$ | $>3.0 \times 10^6$ | $2.7 \times 10^6$ |
| 7 days | $>3.0 \times 10^6$ | $2.6 \times 10^2$ | $4.5 \times 10^2$ | $1.6 \times 10^3$ | $>3.0 \times 10^6$ | $>3.0 \times 10^6$ |
| 14 days | $>3.0 \times 10^6$ | $2.1 \times 10^2$ | $1.4 \times 10^3$ | $4.5 \times 10^2$ | $>3.0 \times 10^6$ | $>3.0 \times 10^6$ |

Content of Surviving Microorganisms per Gram of Sample (CFU/g) After Contamination

| | Number of surviving microorganisms per g of contaminated sample in the batch after: | | | |
|---|---|---|---|---|
| Microorganisms | Molds I | Molds II | Gram-negative bacteria | Gram-positive bacteria |
| Inoculation | $2.2 \times 10^4$ | $2.5 \times 10^4$ | $2.7 \times 10^4$ | $2.1 \times 10^4$ |
| 1 day | $1.3 \times 10^4$ | $2.5 \times 10^4$ | $>3.0 \times 10^6$ | $6.0 \times 10^4$ |
| 3 days | $4.7 \times 10^3$ | $1.2 \times 10^4$ | $>3.0 \times 10^6$ | $1.1 \times 10^6$ |
| 7 days | $2.5 \times 10^4$ | $2.0 \times 10^4$ | $>3.0 \times 10^6$ | $>2.0 \times 10^6$ |
| 14 days | $2.0 \times 10^4$ | $5.0 \times 10^4$ | $>3.0 \times 10^6$ | $1.3 \times 10^6$ |

Addition of 1 g/l of Calcium Acetate

Content of Surviving Microorganisms per Gram of Sample (CFU/g) After Contamination

| | Number of surviving microorganisms per g of contaminated sample in the batch after: | | | | | |
|---|---|---|---|---|---|---|
| Microorganisms | Lactic acid bacteria | Clostridia | Bacilli | Thermophilic bacilli | Acetic acid bacteria | Yeasts |
| Inoculation | $2.7 \times 10^4$ | $2.9 \times 10^4$ | $3.3 \times 10^4$ | $1.3 \times 10^4$ | $2.8 \times 10^4$ | $2.6 \times 10^4$ |
| 1 day | $5.6 \times 10^5$ | $3.7 \times 10^3$ | $1.6 \times 10^3$ | $2.1 \times 10^3$ | $8.4 \times 10^5$ | $1.3 \times 10^6$ |
| 3 days | $>3.0 \times 10^6$ | $3.2 \times 10^3$ | $1.0 \times 10^3$ | $6.0 \times 10^2$ | $>3.0 \times 10^6$ | $2.5 \times 10^6$ |
| 7 days | $>3.0 \times 10^6$ | $<100$ | $1.8 \times 10^3$ | $<10$ | $>3.0 \times 10^6$ | $>3.0 \times 10^6$ |
| 14 days | $2.4 \times 10^4$ | $<10$ | $1.8 \times 10^3$ | $<10$ | $1.5 \times 10^6$ | $>3.0 \times 10^6$ |

Content of Surviving Microorganisms per Gram of Sample (CFU/g) After Contamination

| Microorganisms | Molds I | Molds II | Gram-negative bacteria | Gram-positive bacteria |
|---|---|---|---|---|
| Inoculation | $2.2 \times 10^4$ | $2.5 \times 10^4$ | $2.7 \times 10^4$ | $2.1 \times 10^4$ |
| 1 day | $1.1 \times 10^4$ | $1.5 \times 10^4$ | $1.7 \times 10^4$ | $1.1 \times 10^5$ |
| 3 days | $2.2 \times 10^3$ | $1.2 \times 10^4$ | $1.3 \times 10^4$ | $9.0 \times 10^4$ |
| 7 days | $7.6 \times 10^3$ | $>1.0 \times 10^5$ | $2.2 \times 10^3$ | $6.7 \times 10^3$ |
| 14 days | $4.5 \times 10^4$ | $3.5 \times 10^4$ | <100 | $5.9 \times 10^3$ |

Addition of 1 g/l of Calcium Sorbate

Content of Surviving Microorganisms per Gram of Sample (CFU/g) After Contamination

| Microorganisms | Lactic acid bacteria | Clostridia | Bacilli | Thermophilic bacteria | Acetic acid bacilli | Yeasts |
|---|---|---|---|---|---|---|
| Inoculation | $2.7 \times 10^4$ | $2.9 \times 10^4$ | $3.3 \times 10^4$ | $1.3 \times 10^4$ | $2.8 \times 10^4$ | $2.6 \times 10^4$ |
| 1 day | $3.4 \times 10^3$ | $2.2 \times 10^3$ | $2.8 \times 10^3$ | $1.4 \times 10^3$ | $1.5 \times 10^4$ | $2.3 \times 10^4$ |
| 3 days | $2.0 \times 10^3$ | <100 | $1.8 \times 10^3$ | $5.0 \times 10^2$ | $1.4 \times 10^4$ | $1.0 \times 10^4$ |
| 7 days | <100 | <10 | $1.3 \times 10^3$ | <10 | $2.0 \times 10^4$ | <100 |
| 14 days | <10 | <10 | $1.2 \times 10^3$ | <10 | $1.3 \times 10^5$ | <10 |

Content of Surviving Microorganisms per Gram of Sample (CFU/g) After Contamination

| Microorganisms | Molds I | Molds II | Gram-negative bacteria | Gram-positive bacteria |
|---|---|---|---|---|
| Inoculation | $2.2 \times 10^4$ | $2.5 \times 10^4$ | $2.7 \times 10^4$ | $2.1 \times 10^4$ |
| 1 day | $3.9 \times 10^3$ | $6.5 \times 10^3$ | $1.7 \times 10^4$ | $2.1 \times 10^4$ |
| 3 days | <100 | <100 | $1.0 \times 10^4$ | $6.4 \times 10^3$ |
| 7 days | <10 | <10 | $1.9 \times 10^3$ | <10 |
| 14 days | <10 | <10 | $2.7 \times 10^3$ | <10 |

Addition of 1 g/l of Calcium Double Salts of Sorbic Acid and Acetic Acid

Content of Surviving Microorganisms per Gram of Sample (CFU/g) After Contamination

| Microorganisms | Lactic acid bacteria | Clostridia | Bacilli | Thermophilic bacilli | Acetic acid bacteria | Yeasts |
|---|---|---|---|---|---|---|
| Inoculation | $2.7 \times 10^4$ | $2.9 \times 10^4$ | $3.3 \times 10^4$ | $1.3 \times 10^4$ | $2.8 \times 10^4$ | $2.6 \times 10^4$ |
| 1 day | $5.5 \times 10^3$ | $7.0 \times 10^2$ | $2.5 \times 10^3$ | $2.3 \times 10^3$ | $2.5 \times 10^4$ | $1.3 \times 10^4$ |
| 3 days | <100 | <100 | $1.7 \times 10^3$ | $1.1 \times 10^3$ | $6.5 \times 10^3$ | $3.4 \times 10^3$ |
| 7 days | <10 | <10 | $1.7 \times 10^3$ | $1.0 \times 10^2$ | $1.7 \times 10^5$ | <100 |
| 14 days | <10 | <10 | $1.4 \times 10^3$ | <10 | $1.6 \times 10^5$ | <10 |

Content of Surviving Microorganisms per Gram of Sample (CFU/g) After Contamination

| Microorganisms | Molds I | Mold II | Gram-negative bacteria | Gram-positive bacteria |
|---|---|---|---|---|
| Inoculation | $2.2 \times 10^4$ | $2.5 \times 10^4$ | $2.7 \times 10^4$ | $2.1 \times 10^4$ |
| 1 day | $3.7 \times 10^3$ | $4.4 \times 10^3$ | $9.0 \times 10^3$ | $2.5 \times 10^4$ |
| 3 days | $5.0 \times 10^2$ | <100 | $3.2 \times 10^3$ | $6.2 \times 10^3$ |
| 7 days | $1.0 \times 10^2$ | <10 | $1.5 \times 10^3$ | $2.7 \times 10^3$ |
| 14 days | <100 | <10 | $4.2 \times 10^4$ | <10 |

The results of these tests show that the calcium double salt of acetic acid and sorbic acid acts well and persistently against all microorganisms used except for acetic acid bacteria and bacilli. The growth of Gram-negative bacteria is substantially inhibited. In the case of contamination, this double salt also acts surprisingly better than calcium acetate (in particular against lactic acid bacteria, yeasts, molds and Gram-positive bacteria) or calcium sorbate (in particular against lactic acid bacteria) used alone.

Addition of 1 g/l of Calcium Formate

Content of Surviving Microorganisms per Gram of Sample (CFU/g) After Contamination

| Microorganisms | Number of surviving microorganisms per g of contaminated sample in the batch after: | | | | | |
|---|---|---|---|---|---|---|
| | Lactic acid bacteria | Clostridia | Bacilli | Thermophilic bacilli | Acetic acid bacteria | Yeasts |
| Inoculation | $2.7 \times 10^4$ | $2.9 \times 10^4$ | $3.3 \times 10^4$ | $1.3 \times 10^4$ | $2.8 \times 10^4$ | $2.6 \times 10^4$ |
| 1 day | $4.4 \times 10^3$ | $4.0 \times 10^2$ | $1.7 \times 10^3$ | $2.3 \times 10^3$ | $8.7 \times 10^5$ | $7.4 \times 10^5$ |
| 3 days | $2.5 \times 10^4$ | $2.0 \times 10^2$ | $1.5 \times 10^3$ | $8.0 \times 10^2$ | $2.5 \times 10^6$ | $1.0 \times 10^6$ |
| 7 days | $>3.0 \times 10^6$ | <100 | $1.4 \times 10^3$ | $6.0 \times 10^2$ | $>3.0 \times 10^6$ | $>3.0 \times 10^6$ |
| 14 days | $>3.0 \times 10^6$ | 10 | $1.7 \times 10^3$ | <10 | $>3.0 \times 10^6$ | $>3.0 \times 10^6$ |

Content of Surviving Microorganisms per Gram of Sample (CFU/g) After Contamination

| Micro-organisms | Number of surviving microorganisms per g of contaminated sample in the batch after: | | | |
|---|---|---|---|---|
| | Molds I | Mold II | Gram-negative bacteria | Gram-positive bacteria |
| Inoculation | $2.2 \times 10^4$ | $2.5 \times 10^4$ | $2.7 \times 10^4$ | $2.1 \times 10^4$ |
| 1 day | $4.1 \times 10^3$ | $1.0 \times 10^4$ | $1.5 \times 10^4$ | $2.2 \times 10^4$ |
| 3 days | $2.9 \times 10^3$ | $1.5 \times 10^3$ | $3.6 \times 10^3$ | $8.9 \times 10^3$ |
| 7 days | $1.9 \times 10^3$ | $>3.0 \times 10^4$ | $2.3 \times 10^3$ | $4.6 \times 10^3$ |
| 14 days | $2.6 \times 10^3$ | $3.9 \times 10^5$ | 75 | $2.0 \times 10^3$ |

Addition of 1 g/l of Calcium Double Salt of Sorbic Acid and Formic Acid

Content of Surviving Microorganisms per Gram of Sample (CFU/g) After Contamination

| Microorganisms | Number of surviving microorganisms per g of contaminated sample in the batch after: | | | | | |
|---|---|---|---|---|---|---|
| | Lactic acid bacteria | Clostridia | Bacilli | Thermophilic bacilli | Acetic acid bacteria | Yeasts |
| Inoculation | $2.7 \times 10^4$ | $2.9 \times 10^4$ | $3.3 \times 10^4$ | $1.3 \times 10^4$ | $2.8 \times 10^4$ | $2.6 \times 10^4$ |
| 1 day | $3.9 \times 10^3$ | $1.1 \times 10^3$ | $3.2 \times 10^3$ | $2.0 \times 10^3$ | $2.1 \times 10^4$ | $1.3 \times 10^4$ |
| 3 days | $1.5 \times 10^3$ | <100 | $1.8 \times 10^3$ | $3.0 \times 10^2$ | $1.6 \times 10^4$ | $4.3 \times 10^3$ |
| 7 days | <10 | 100 | $1.7 \times 10^3$ | <10 | $7.6 \times 10^3$ | <100 |
| 14 days | <10 | <10 | $1.8 \times 10^3$ | <10 | $2.6 \times 10^4$ | <10 |

Content of Surviving Microorganisms per Gram of Sample (CFU/g) After Contamination

| Micro-organisms | Number of surviving microorganisms per g of contaminated sample in the batch after: | | | |
|---|---|---|---|---|
| | Molds I | Mold II | Gram-negative bacteria | Gram-positive bacteria |
| Inoculation | $2.2 \times 10^4$ | $2.5 \times 10^4$ | $2.7 \times 10^4$ | $2.1 \times 10^4$ |
| 1 day | $3.8 \times 10^3$ | $3.9 \times 10^3$ | $1.7 \times 10^4$ | $2.1 \times 10^4$ |
| 3 days | $2.0 \times 10^2$ | <100 | $2.5 \times 10^3$ | $8.5 \times 10^3$ |
| 7 days | 25 | <10 | $2.0 \times 10^3$ | $6.8 \times 10^2$ |
| 14 days | 10 | <10 | <10 | <10 |

The results of these tests show the calcium double salt of formic acid and sorbic acid acts well and persistently against all microorganisms used, except for acetic acid bacteria and bacilli. In the case of contamination, this double salt also acts surprisingly better than calcium formate (in particular against lactic acid bacteria, yeasts and molds) or calcium sorbate (in particular against Gram-negative bacteria) used alone.

What is claimed is:

1. A calcium double salt of organic (preservative) acids of formula I:

$$Ca(R^1)(R^2) \qquad (I)$$

where $R^1$ and $R^2$ are different and are each OOC—$R^3$, where $R^3$=saturated or monounsaturated or polyunsaturated $C_1$–$C_5$-alkyl, $C_1$–$C_5$-hydroxyalkyl or phenyl.

2. A salt as claimed in claim 1, wherein $R^3$ is methyl, ethyl, hydroxyethyl, propyl, 1,3-hexadienyl (=sorbate anion) or phenyl.

3. A salt as claimed in claim 1, wherein $R^1$ is propionate and $R^2$ is sorbate.

4. A process for preparing double salts of organic acids as claimed in claim 1, which comprises mixing a solution of the calcium salt of the carboxylic acid which is more soluble in water with a solution of the alkali metal salt of the second carboxylic acid and separating off and drying the resulting precipitate.

5. The process as claimed in claim 4, wherein the solutions used are as saturated as possible.

6. A method of preserving foods, drugs, feeds, silage, brewers' spent grains, pomace, food wastes, brewers' yeast, distillation residues, cosmetics, leather and industrial products which method comprises mixing a salt as claimed in claim 1 with foods, drugs, feeds, silage, brewers' spent grains, pomace, food wastes, brewers' yeast, distillation residues, cosmetics, leather and industrial products.

7. A food which comprises a salt as claimed in claim 1.
8. A drug which comprises a salt as claimed in claim 1.
9. A feed which comprises a salt as claimed in claim 1.
10. A silage which comprises a salt as claimed in claim 1.
11. A brewers' spent grain which comprises a salt as claimed in claim 1.
12. A pomace which comprises a salt as claimed in claim 1.
13. A food waste which comprises a salt as claimed in claim 1.

14. A brewers' yeast which comprises a salt as claimed in claim 1.

15. A distillation residue which comprises a salt as claimed in claim 1.

16. A cosmetic which comprises a salt as claimed in claim 1.

17. A fat emulsion which comprises a salt as claimed in claim 1.

18. An industrial product (film, fungistatic coating) which comprises a salt as claimed in claim 1.

19. A preparation which comprises one or more of the following substances:

starch, starch derivative, cellulose ether, polysaccharide, polyvinyl alcohol and a salt as claimed in claim 1.

* * * * *